(12) United States Patent
Maggioni et al.

(10) Patent No.: US 11,497,859 B2
(45) Date of Patent: Nov. 15, 2022

(54) SAFETY SYRINGE HAVING A RETRACTING NEEDLE AND BEING PRE-FILLABLE WITH TWO ACTIVE INGREDIENTS

(71) Applicant: TECNEDIL INTERNATIONAL S.R.L., Milan (IT)

(72) Inventors: Andrea Maggioni, Correzzana (IT); Chiara Maggioni, Brugherio (IT); Tarcisio Maggioni, Brugherio (IT)

(73) Assignee: TECNEDIL INTERNATIONAL S.R.L., Milan (IT)

( * ) Notice: Subject to any disclaimer, the term of this patent is extended or adjusted under 35 U.S.C. 154(b) by 580 days.

(21) Appl. No.: 16/479,142

(22) PCT Filed: Jan. 16, 2018

(86) PCT No.: PCT/EP2018/051034
§ 371 (c)(1),
(2) Date: Jul. 18, 2019

(87) PCT Pub. No.: WO2018/134211
PCT Pub. Date: Jul. 26, 2018

(65) Prior Publication Data
US 2019/0351150 A1    Nov. 21, 2019

(30) Foreign Application Priority Data
Jan. 19, 2017 (IT) .................. 102017000005872

(51) Int. Cl.
*A61M 5/32* (2006.01)
*A61M 5/19* (2006.01)
(Continued)

(52) U.S. Cl.
CPC ............ *A61M 5/3232* (2013.01); *A61M 5/19* (2013.01); *A61M 5/284* (2013.01); *A61M 5/286* (2013.01);
(Continued)

(58) Field of Classification Search
CPC .... A61M 5/284; A61M 5/286; A61M 5/3294; A61M 5/3232; A61M 5/285
See application file for complete search history.

(56) References Cited

U.S. PATENT DOCUMENTS 3,380,451 A  *  4/1968  Porter .................. A61M 5/284
                                                         604/90
2004/0147876 A1   6/2004  Maggioni
2013/0035664 A1   2/2013  Mojdehbakhsh et al.

FOREIGN PATENT DOCUMENTS

WO            84/01510 A1    4/1984
WO       WO-8401510 A1  *  4/1984  .......... A61M 5/3243

OTHER PUBLICATIONS

WO8401510A1 Description Translation, generated on Dec. 21, 2021. (Year: 1984).*
(Continued)

*Primary Examiner* — Brandy S Lee
*Assistant Examiner* — Melissa A Snyder
(74) *Attorney, Agent, or Firm* — Themis Law

(57) ABSTRACT

The single-use safety syringe having a manual and/or automatic retracting needle preventing re-use thereof comprises a needle, a piston with a tightening seal and a cylindrical body having, at an end thereof, a connector provided with a calibrated attaching hole for the needle and open, at another end thereof, for inserting the piston, comprising, internally of the cylindrical body, a separating seal of a first chamber comprised between the separating seal and the connector in which a first active ingredient is positioned and a second chamber comprised between the separating seal and the tightening seal in which a second active ingredient is positioned, the separating seal having a connecting channel between the first and second chamber, closed by a pressure limiting valve, first engaging means further being provided, activatable for engaging the separating seal to the needle and
(Continued)

second engaging means activatable for engaging the separating seal to the piston.

10 Claims, 2 Drawing Sheets

(51) Int. Cl.
*A61M 5/28* (2006.01)
*A61M 5/31* (2006.01)
(52) U.S. Cl.
CPC ........ *A61M 5/3221* (2013.01); *A61M 5/3234* (2013.01); *A61M 5/3294* (2013.01); *A61M 2005/3123* (2013.01); *A61M 2005/3128* (2013.01); *A61M 2005/3231* (2013.01); *A61M 2207/00* (2013.01)

(56) References Cited

OTHER PUBLICATIONS

International Search Report and Written Opinion issued in corresponding International Patent Application No. PCT/EP2018/051034 dated Apr. 9, 2018.

\* cited by examiner

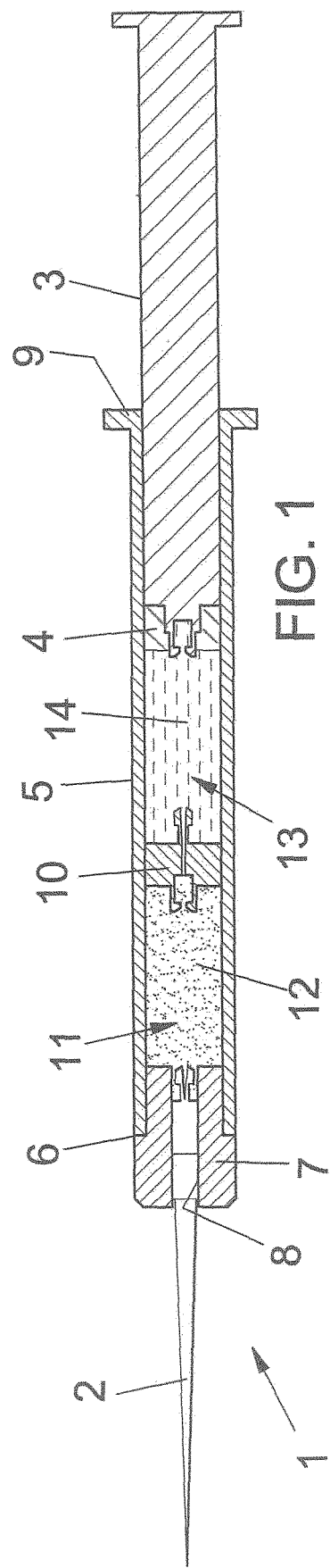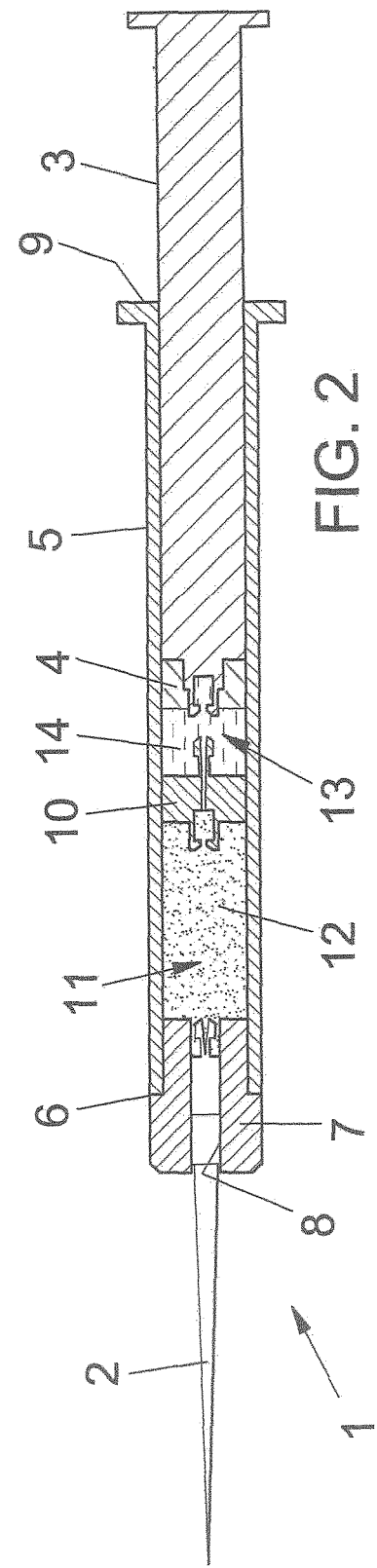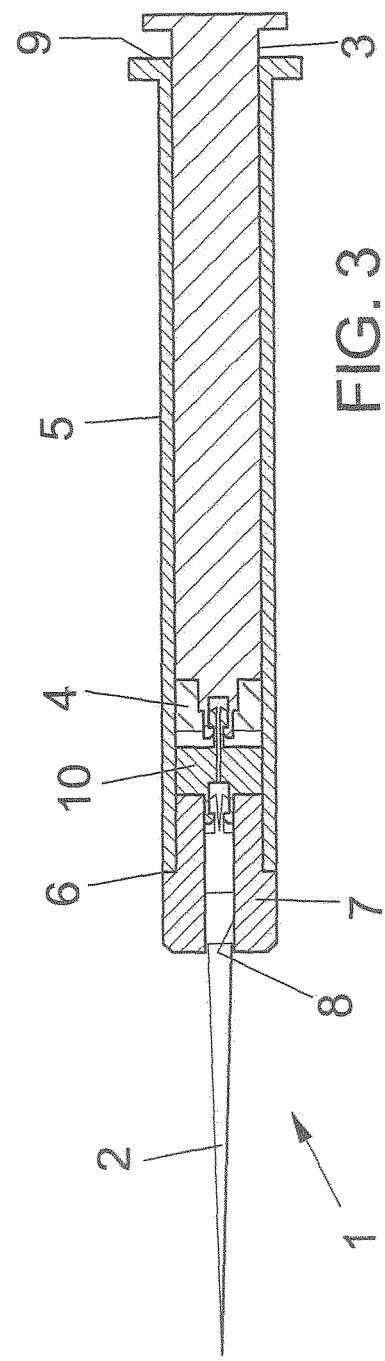

SAFETY SYRINGE HAVING A RETRACTING NEEDLE AND BEING PRE-FILLABLE WITH TWO ACTIVE INGREDIENTS

CROSS REFERENCE TO RELATED APPLICATIONS

This is a U.S. National Phase application under 35 U.S.C. § 371 of International Patent Application No. PCT/EP2018/051034, filed Jan. 16, 2018, which claims priority of Italian Patent Application No. 102017000005872, filed Jan. 19, 2017. The entire contents of which are hereby incorporated by reference.

FIELD OF TECHNOLOGY

The present invention relates to a single-use safety syringe having a manual and/or automatic retracting needle for preventing re-use thereof.

BACKGROUND

As is known, a problem when using single-use syringes consists in the possibility of a re-use thereof and in the risk that following use the needle can injure the operator.

Safety systems have therefore been devised which include special elastic recall means which cause the automatic retraction of the needle at end of use.

Usually the safety systems are installed in syringes that are filled by the operator only at the moment of the injection.

The operator frequently has to create the filling means by mixing a liquid active ingredient with a freeze-dried active ingredient.

In this case the success of the operation is subordinated to the ability of the operator that first has to open the vial containing the liquid active ingredient, then aspirate, using the syringe, the liquid active ingredient, then inject the active ingredient into the container containing the freeze-dried active ingredient, then aspirate, using the syringe, the filling means thus realized.

Before carrying out the injection the operator also has to expel, by activating the piston of the syringe, the air present in the chamber of the syringe into which the filling means has been aspirated.

SUMMARY

Therefore, the technical task of the present invention is to provide a single-use safety syringe having a manual and/or automatic retracting needle for preventing re-use thereof which obviates the above-described technical drawbacks of the prior art.

Within the scope of this technical task an aim of the invention is to realize a single-use safety syringe with a manual and/or automatic retracting needle for preventing re-use thereof which is pre-fillable with two active ingredients so as to be ready for the injection of the filling means into the patient without the need of a laborious preliminary preparation process by the operator.

A further aim of the invention is to realize a single-use safety syringe with a manual and/or automatic retracting needle pre-fillable with two active ingredients that is extremely reliable and safe in use.

A further and not least aim of the invention is to realize a single-use safety syringe with a manual and/or automatic retracting needle pre-fillable with two active ingredients that is constructionally simple and economical.

The technical task, as well as these and other aims, according to the present invention, are attained by realizing a single-use safety syringe having a manual and/or automatic retracting needle for preventing re-use thereof, comprising a needle, a piston provided with a tightening seal and a cylindrical body having, at an end thereof, a connector provided with a calibrated attaching hole for said needle and open, at another end thereof, for inserting said piston, characterised in that it comprises, internally of said cylindrical body, a separating seal of a first chamber comprised between said separating seal and said connector in which a first active ingredient is positioned and a second chamber comprised between said separating seal and said tightening seal in which a second active ingredient is positioned, said separating seal having a connecting channel between said first and second chamber, closed by a pressure limiting valve, first engaging means further being provided, activatable for engaging said separating seal to said needle and second engaging means activatable for engaging said separating seal to said piston. Said first active ingredient is preferably freeze-dried and said second active ingredient is liquid.

Said first engaging means preferably comprise elastically yielding catches snap-engageable with corresponding counter catches.

Said second engaging means preferably comprise elastically yielding catches 23 snap-engageable with corresponding counter catches.

The present invention also relates to a method for assembling a single-use safety syringe having a manual and/or automatic retracting needle, characterised in that it comprises the following steps:
  introducing the separating seal into the cylindrical body;
  arranging the cylindrical body in a vertical position with the open end thereof facing upwards and loading the second active ingredient into the second chamber;
  inserting the piston into the cylindrical body;
  overturning the cylindrical body and, with a tool inserted through said calibrated hole of said connector, exerting a push against said separating seal so that an intervention pressure of said limiting valve is reached internally of said second chamber for expulsion of the air present in said second chamber;
  loading the first active ingredient in the first chamber through said calibrated hole of said connector; and
  applying the needle to said connector.

Other characteristics of the present invention are further defined in the dependent claims.

Further characteristics and advantages of the invention will more fully emerge from the description of a preferred but not exclusive embodiment of the single-use safety syringe having a manual and/or automatic retracting needle pre-fillable with two active ingredients according to the invention, illustrated by way of non-limiting example in the accompanying figures of the drawings, in which:

BRIEF DESCRIPTION OF THE DRAWINGS

FIG. 1, FIG. 2 and FIG. 3 show an axial section of the syringe in the sequence of configurations undertaken up to completion of the injection of the filling means;

DETAILED DESCRIPTION

Figure 4:
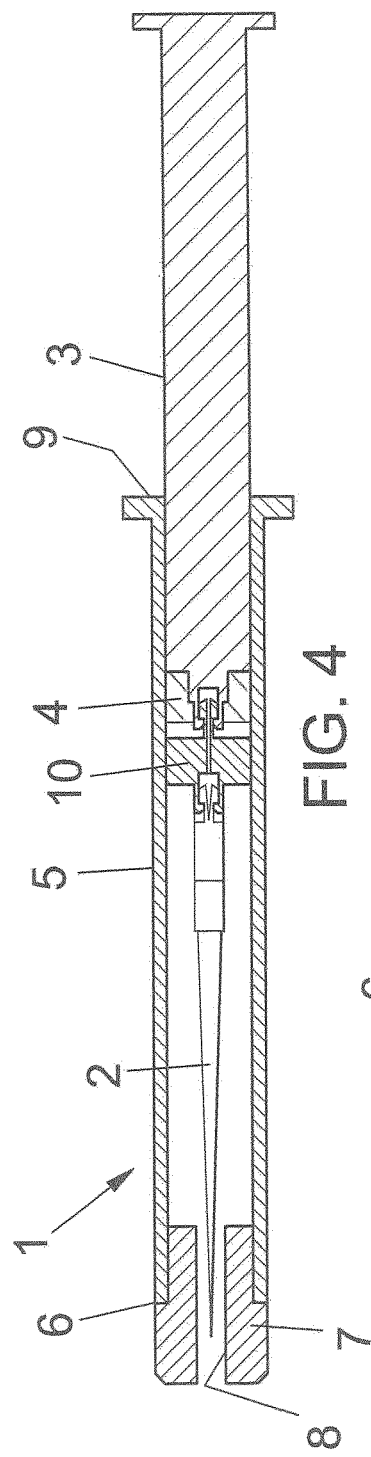
FIG. 4 shows the configuration of the syringe with the needle retracted following completion of the injection by effect of the retraction of the piston carried out by the operator.
Figure 5:
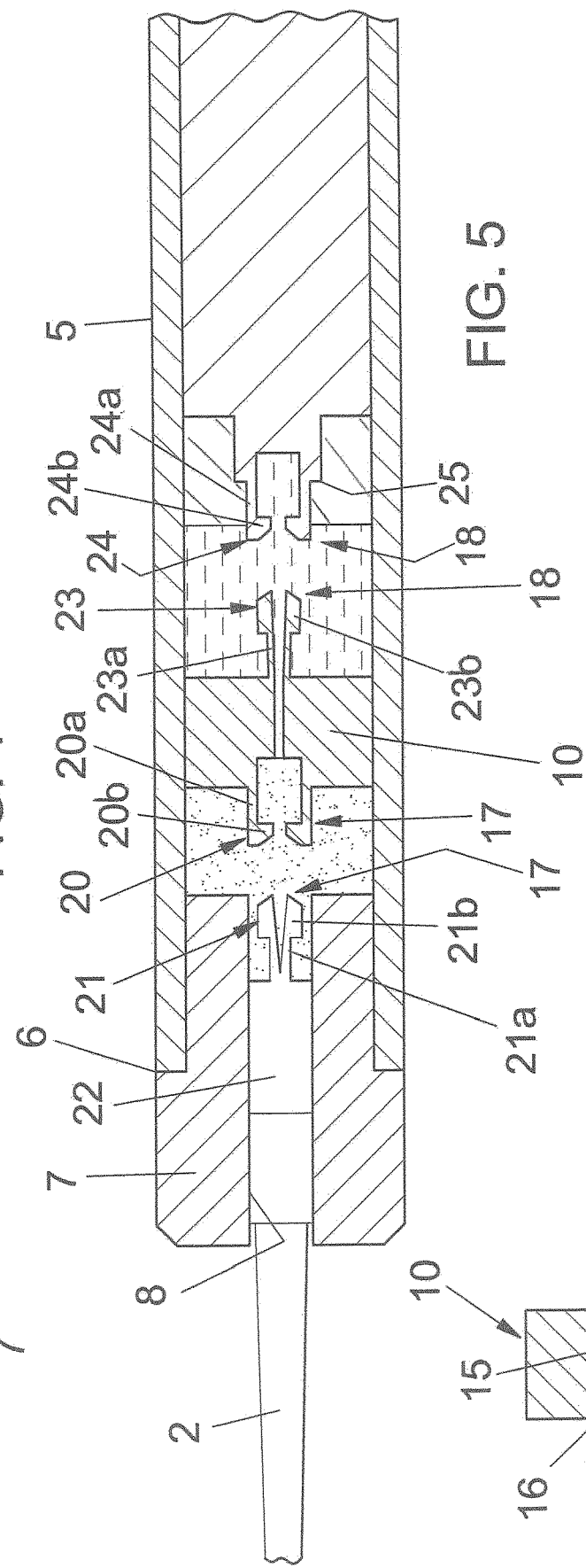
FIG. 5 shows an axial section of a magnified detail of the syringe in a configuration undertaken during the injection of the filling means.
Figure 6:
FIG. 6 shows an axial section of the separating seal.

In the following description, the term "front" and the term "rear" are used with reference to a front-rear direction which goes from the tip of the needle towards the piston of the syringe.

With reference to the figures mentioned, a single-use safety syringe having a pre-fillable automatic retracting needle with two active ingredients is shown, generally indicated with the reference number 1.

The syringe 1 comprises a needle 2, a piston 3 provided with a tightening seal 4 and a cylindrical body 5 in which the piston 3 is slidable.

The cylindrical body 5 has, at an end 6 thereof, a connector 7 provided with a calibrated attaching hole 8 for the needle 2 while the other end 9 of the cylindrical body 5 is open for inserting the piston 3.

More precisely, the needle 2 has a shank 22 slidably engaged in the calibrated hole 8 in the movement direction of the piston 4.

By way of example, the connector 7 can be a luer-lock connector.

Internally of said cylindrical body 5, a separating seal 10 is advantageously comprised which separates a first chamber 11, comprised between the separating seal 10 and the connector 7 in which a first active ingredient 12 is positioned, and a second chamber 13, comprised between the separating seal 10 and the tightening seal 4 in which a second active ingredient 14 is positioned.

The first active ingredient consists of a freeze-dried substance while the second active ingredient consists of a liquid.

The separating seal 10 has a connecting channel 15 between the first chamber 11 and second chamber 13, closed by a pressure limiting valve 16.

The separating seal 10 has a friction and form coupling with said cylindrical body 5 and is sealedly slidable internally of the cylindrical body 5 in the movement direction of the piston 3.

In particular, the separating seal 10 is realized using the same rubber material as the tightening seal 4, while the cylindrical body 5 with which the tightening seal 4 and the separating seal 10 are slidably engaged is made of plastic and more precisely copolymer.

The connecting channel 15 in the separating seal 10 is formed by a through-hole that extends coaxially to the cylindrical body 5.

The pressure limiting valve 16 comprises an elastic membrane obturator 19 openable by deformation.

The membrane obturator 19 is welded along all or a part of a perimeter thereof to the separating seal 10.

In particular, in the illustrated case, the membrane obturator 19 is formed by a disc welded at a portion of the perimeter edge thereof to the front end of the connecting channel 15.

Alternatively, the membrane obturator 19 can be formed for example by two half-discs arranged with straight perimeter edges thereof juxtaposed and with the arched perimeter edges thereof welded to the front end of the connecting channel 15.

Other embodiments of the pressure limiting valve 16 are also conceivable, and in particular it can also be positioned internally of the connecting channel 15 or at the rear end of the connecting channel 15.

Advantageously, first engaging means 17 are further provided activatable for engaging the separating seal 10 to the needle 2, and second engaging means 18 activatable for engaging the separating seal 10 to the piston 3.

The first engaging means 17 comprise elastically yielding catches 20 snap-engageable with corresponding counter catches 21.

The catches 20, integrated with the separating seal 10, are frontally prolonged to the separating seal 10 and are distributed about the front end of the connecting channel 15, while the counter catches 21, integrated with the needle 2, are prolonged posteriorly of the shank 22 of the needle 2 and are distributed about the rear end of the hole of the needle 2.

The catches 20 and the counter catches 21 are each formed by a flexible stalk 20a, 21a and a hooking head 20b, 21b.

The flexible stalk 20a has a depression enabling an unbalancing of the shank 22 and an inclination of the needle 2 on the vertical axis thereof.

The second engaging means 18 also comprise elastically yielding catches 23 snap-engageable with corresponding counter catches 24.

The catches 23, integrated with the separating seal 10, prolong posteriorly of the separating seal 10 and are distributed about the rear end of the connecting channel 15, while the counter catches 24, integrated with the piston 3, are prolonged frontally of the tightening seal 4, crossing a through-opening 25 of the tightening seal 4.

The catches 23 and the counter catches 24 are each formed by a flexible stalk 23a, 24a and a hooking head 23b, 24b.

The assembly of the syringe takes place in the following way.

The separating seal 10 is initially introduced into the cylindrical body 5.

The cylindrical body 5 is then arranged in a vertical position with the open end thereof facing upwards and the main liquid active ingredient is loaded into the second chamber 13.

At this point, the piston 3, suitably predisposed with the tightening seal 4, is inserted into the cylindrical body 5.

Subsequently, the cylindrical body 5 is overturned and kept blocked in the overturned position, and a rod-shaped tool (not illustrated) suitably inserted through the calibrated hole 8 of the connector 7 is used to exert a push against the separating seal 10 so as to increase the pressure present in the second chamber 13 until reaching the operating pressure of the limiting valve 16.

In this situation the second chamber 13, through the open limiting valve 16, bleeds the air present internally thereof.

After the removal of the tool, the limiting valve 16 is re-closed automatically, resetting the isolation between the first chamber 11 and the second chamber 13. At this point, the freeze-dried active ingredient is loaded into the first chamber 11, by means of a special cannula (not illustrated) introduced through the calibrated Lastly, after the removal of the cannula, the needle 2 is fixed to the connector 7. The operating function of the syringe 1 for the injection is carried out in the following steps.

The piston 3 is pressed with the tightening seal 4 on the liquid active ingredient present in the second chamber 13.

The push on the piston 3 generates, internally of the second chamber 13, a pressure so as to open the limiting valve 16 so that while the piston 3 advances towards the separating seal 10 the liquid active ingredient flows into the first chamber 11 where it mixes with the freeze-dried active ingredient.

As the piston 3 is advanced, the second chamber 13 progressively empties and at a certain point the counter-catches 24 engage with the catches 23, determining the hooking between the separating seal 10 and the piston 3.

At this point, continuing with the pushing on the piston 3, the group formed by the piston 3—tightening seal 4—separating seal 10 advances in constrained formation towards the needle 2.

As the group formed by the piston 3—tightening seal 4—separating seal 10 is advanced, the mixture flows through the needle 2 and the first chamber 11 progressively empties until at a certain point the catches 20 engage with the counter catches 21, causing the hooking between the needle 2 and the assembly formed by the piston 3—tightening seal 4—separating seal 10.

Once the injection has been completed the operator retracts the piston 3 which draws with it not only the tightening seal 4 and the separating seal 10, but also the needle 2 which returns completely internally of the cylindrical body 5 in the safety position.

In a different embodiment of the invention, not illustrated, the retracting of the needle can be automatically induced, when the operator releases the piston, by an elastic recall element opportunely positioned in the cylindrical body.

The single-use safety syringe having a manual and/or automatic retracting needle for preventing re-use thereof as conceived herein is susceptible of numerous modifications and variants, all falling within the scope of the inventive concept; furthermore, all the details are replaceable by technically equivalent elements. In practice the materials used, as well as the dimensions, can be any according to the needs and the state of the art.

The invention claimed is:

1. A single-use safety syringe having a manually and/or or automatic retracting needle for preventing re-use thereof, comprising:
    a needle;
    a piston provided with a tightening seal;
    a cylindrical body having, at an end thereof, a connector provided with a calibrated hole receiving said needle and being open, at another end thereof, for inserting said piston;
    a separating seal arranged internally of said cylindrical body, said separating seal separating a first chamber comprised between said separating seal and said connector, a first active ingredient being positioned inside said first chamber, and a second chamber comprised between said separating seal and said tightening seal, a second active ingredient being positioned inside said second chamber, said separating seal having a connecting channel between said first and second chamber, said connecting channel being closed by a pressure limiting valve;
    first engaging means activatable for engaging said separating seal to said needle, said first engaging means comprising a first member extending from said separating seal toward said needle and a second member extending from said needle toward said separating seal; and
    second engaging means activatable for engaging said separating seal to said piston, said second engaging means comprising a third member extending directly from said piston toward said separating seal and a fourth member extending from said separating seal toward said piston.

2. The single-use safety syringe according to claim 1, wherein said separating seal has a friction and shape coupling with said cylindrical body and is sealedly slidable internally thereof in a movement direction of said piston.

3. The single-use safety syringe according to claim 1, wherein said pressure limiting valve comprises an elastic membrane obturator openable by deformation.

4. The single-use safety syringe according to claim 3, wherein said membrane obturator is welded along all or a part of a perimeter thereof to said separating seal.

5. The single-use safety syringe according to claim 1, wherein said first engaging means member comprises elastically yielding catches snap-engageable with corresponding counter catches comprised in said second member.

6. The single-use safety syringe according to claim 5, wherein said needle has a shank engaged in said calibrated hole, said needle being slidable in a movement direction of said piston, said catches being hook-shaped and prolonged frontally of said separating seal, said counter catches being hook-shaped and prolonged posteriorly of said shank.

7. The single-use safety syringe according to claim 1, wherein said third member comprise catches that are snap-engageable with corresponding counter-catches comprised in the fourth member.

8. The single-use safety syringe according to claim 1, wherein said connecting channel is formed by a through-hole that is coaxial to said cylindrical body.

9. The single-use safety syringe according to claim 1, wherein said first active ingredient is freeze-dried and said second active ingredient is liquid.

10. A method for assembling a single-use safety syringe having a manually or automatic retracting needle for preventing re-use thereof, said single-use safety syringe comprising:
    a needle;
    a piston provided with a tightening seal,
    a cylindrical body having, at an end thereof, a connector provided with a calibrated hole receiving said needle and being open, at another end thereof, for inserting said piston;
    a separating seal arranged internally of said cylindrical body and separating a first chamber comprised between said separating seal and said connector, a first active ingredient being positioned inside said first chamber, and a second chamber comprised between said separating seal and said tightening seal, a second active ingredient being positioned inside said second chamber, said separating seal having a connecting channel between said first and second chamber, said connecting channel being closed by a pressure limiting valve; and
    first engaging means activatable for engaging said separating seal to said needle and second means activatable for engaging said separating seal to said piston,
    wherein said first active ingredient is freeze-dried and said second active ingredient is liquid,
    the method comprising the following steps:
    introducing the separating seal into the cylindrical body;
    arranging the cylindrical body in a vertical position with the open end thereof facing upwards and loading the second active ingredient into the second chamber;
    inserting the piston into the cylindrical body;
    overturning the cylindrical body and, with a tool inserted through said calibrated hole of said connector, exerting a push against said separating seal up until an intervention pressure of said limiting valve is reached internally of said second chamber so as to bleed the air present in said second chamber;

loading the first active ingredient in the first chamber through said calibrated hole of said connector; and applying the needle to said connector.

\* \* \* \* \*